(12) United States Patent
Krulevitch et al.

(10) Patent No.: US 11,724,035 B2
(45) Date of Patent: Aug. 15, 2023

(54) INJECTION DEVICE WITH ERGONOMIC HOUSING FORM FACTOR

(71) Applicant: Janssen Pharmaceuticals, Inc., Titusville, NJ (US)

(72) Inventors: Peter Krulevitch, Pleasanton, CA (US); Michael Cannamela, Atlantic Highlands, NJ (US); Nick Foley, Edinburgh (GB); James McLusky, Edinburgh (GB); Jimmy Mower, Edinburgh (GB); Scott Martin, Edinburgh (GB); James Glencross, Edinburgh (GB)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 251 days.

(21) Appl. No.: 16/940,672

(22) Filed: Jul. 28, 2020

(65) Prior Publication Data

US 2021/0030967 A1    Feb. 4, 2021

Related U.S. Application Data

(60) Provisional application No. 62/880,838, filed on Jul. 31, 2019.

(51) Int. Cl.
*A61M 5/31*    (2006.01)

(52) U.S. Cl.
CPC ........ *A61M 5/3137* (2013.01); *A61M 5/3134* (2013.01); *A61M 2202/0007* (2013.01); *A61M 2202/30* (2013.01); *A61M 2205/586* (2013.01)

(58) Field of Classification Search
CPC .............. A61M 5/3137; A61M 5/3134; A61M 2202/0007; A61M 2202/30; A61M 2205/586; A61M 2005/208; A61M 5/3243; A61M 2005/3247; A61M 5/3257; A61M 5/326; A61M 2005/3263; A61M 2005/3264; A61M 2005/2013; A61M 5/2033

See application file for complete search history.

(56) References Cited

U.S. PATENT DOCUMENTS

| | | | |
|---|---|---|---|
| 5,728,074 A | * | 3/1998 | Castellano .......... A61M 5/1723 604/209 |
| 8,021,335 B2 | | 9/2011 | Lesch |
| D697,205 S | | 1/2014 | Schneider |

(Continued)

FOREIGN PATENT DOCUMENTS

| | | |
|---|---|---|
| EP | 3187216 | 7/2017 |
| WO | WO 1998/055168 | 12/1998 |

(Continued)

OTHER PUBLICATIONS

International Search Report dated Sep. 18, 2020; International Application No. PCT/IB2020/057115.

*Primary Examiner* — Katherine H Schwiker
*Assistant Examiner* — Hong-Van N Trinh
(74) *Attorney, Agent, or Firm* — Craig M. Brown

(57) ABSTRACT

An injection device comprises a housing having a proximal end, a distal end and a longitudinal axis extending therebetween. The housing has a hand grip portion with a non-rotationally symmetric cross section about the longitudinal axis of the device at the proximal end of the housing.

33 Claims, 8 Drawing Sheets

(56) References Cited

U.S. PATENT DOCUMENTS

| | | | |
|---|---|---|---|
| D758,567 S | 6/2016 | Wohlfahrt | |
| D758,568 S | 6/2016 | Wohlfahrt | |
| D758,569 S | 6/2016 | Wohlfahrt | |
| D810,281 S | 2/2018 | Holmqvist | |
| D814,022 S | 3/2018 | Boyaval | |
| D819,198 S | 5/2018 | Boyaval | |
| D819,200 S | 5/2018 | Stonecipher | |
| D827,127 S | 8/2018 | Donnelly | |
| D830,538 S | 10/2018 | Guillermo | |
| D861,859 S | 10/2019 | Rapp | |
| D866,757 S | 11/2019 | Diluzio | |
| 2012/0289905 A1* | 11/2012 | Julian | A61M 5/20 604/189 |
| 2015/0297833 A1* | 10/2015 | Henderson | A61M 5/2033 604/135 |
| 2016/0015897 A1* | 1/2016 | Swanson | A61M 5/2033 604/137 |
| 2016/0354580 A1* | 12/2016 | Teoh | A61M 5/1626 |
| 2017/0120016 A1* | 5/2017 | Burkholz | A61M 25/0097 |
| 2021/0030967 A1 | 2/2021 | Krulevitch et al. | |

FOREIGN PATENT DOCUMENTS

| | | |
|---|---|---|
| WO | WO 2014/144096 | 9/2014 |
| WO | WO 2014/164943 | 10/2014 |
| WO | WO 2018/094036 | 5/2018 |
| WO | WO 2021/019443 | 2/2021 |

* cited by examiner

INJECTION DEVICE WITH ERGONOMIC HOUSING FORM FACTOR

FIELD OF INVENTION

The present invention relates to an injection device, in particular to an injection device with an ergonomic housing form factor. For example, the injection device may have a housing with a form factor that promotes proper holding and/or actuation of the device.

BACKGROUND

Injection devices, for example autoinjectors, typically have an elongated shape with a substantially regular cross section along the length of their housing. The lateral cross section of these existing injection devices is typically circular or substantially circular, e.g. having an elliptical or oval form. Such cross sections have rotational symmetry across most or all of the length of the injection device. Conventional injection devices also have symmetrical shapes at both the proximal and distal ends, making it hard to distinguish the proximal end of the device from the distal (injection) end of the device. As a result, conventional injection devices can be grasped and held in a number of different orientations, and some of these orientations may not be advantageous. For example, a user may accidentally hold the device with the injection end against their thumb. Or, alternatively, a user may hold the device with a viewing window on the side of the device facing away from the user, or covered by their hand.

Injection devices are often used by patients for self-administration of pharmacological products. It is often not apparent how these injection devices should be grasped or held. Sometimes, these patients are unwell and thus have restricted movement in their hands and fingers which increases the risk of the injection device being dropped or mishandled. These patients may also have impaired vision and/or cognitive ability and may therefore find it difficult to understand how to hold the device and which end of the device to position against the injection site.

Summary of Disclosure

Embodiments of the invention are defined in the appendant claims. In particular, the invention provides in a first aspect an injection device, comprising:

a housing having a proximal end, a distal end and a longitudinal axis extending therebetween, an injection component including a discharge nozzle, wherein the discharge nozzle is comprised fully within the housing in a pre-injection position, wherein the discharge nozzle in an injection position extends partially or fully from the housing along the longitudinal axis at the distal end of the housing, wherein the housing has a portion with a non-rotationally symmetric cross section about the longitudinal axis at the proximal end of the housing.

The non-rotationally symmetric cross section may exist at other locations along the longitudinal axis, for example at additional locations extending away from the proximal end of the housing.

By having a non-rotationally symmetric cross section about the longitudinal axis at the proximal end of the housing, the injection device will more likely and/or more easily be gripped and handled by a user than prior art injection devices.

The non-rotationally symmetric cross section of the housing may comprise a hand grip portion shaped to fit within a user's hand. The non-rotationally symmetric cross section may be asymmetric. The non-rotationally symmetric cross section may be irregular. A rotationally symmetric cross section would mean that the cross section of the housing would appear the same at one position during at least one partial rotation up to 180 degrees, when compared to its non-rotated position. In contrast, since the cross section is non-rotationally symmetric, it does not fulfil this condition.

The non-rotationally symmetric cross section of the housing may define a hand grip portion. The hand grip portion can be shaped to fit within a user's hand. The hand grip portion is formed at or adjacent the proximal end of the housing, i.e. away from the injection end, and may form a substantial portion of the end of the proximal end of the housing. A portion of the hand grip portion is a curved portion of the housing.

An opposing side of the housing to the curved portion of the hand grip portion may form a flatter shaped part of the cross section relative to the grip portion for receiving fingers of the user's hand when the injection device is being held in the user's hand.

The injection device may comprise a thumb rest portion. This thumb rest portion may be located on the opposing side of the curved portion of the hand grip portion. This thumb rest portion may be a curved surface curving around from the distal end of the device to the curved portion of the hand grip portion. Alternatively or in addition, the thumb rest portion may comprise a planar angled surface with respect to the longitudinal axis of the housing. The thumb rest position may be shaped to receive a thumb of the user's hand. The thumb rest portion may be located on the proximal end of the housing. Both the hand grip portion and the thumb rest portion make it clear to the user that the proximal end is not the needle end of the device, and moreover that this end if the end by which the device should be held.

The injection device may comprise a discharge nozzle protector, wherein the discharge nozzle protector moves between a position entirely covering the discharge nozzle when in the pre-injection position to a retracted position in which the discharge nozzle is partially or fully exposed.

The injection component may be moveable within the housing between the pre-injection position and the injection position. The injection device may comprise a drive mechanism and a trigger, wherein the injection component is moveable automatically upon activation of the drive mechanism.

The trigger may be located at the proximal end of the housing. The trigger may be activatable by being pushed inwards into the housing in a direction substantially along the longitudinal axis. The trigger may be located on a side of the housing and is activatable by being pushed in part inwards into the housing in a radial direction relative to the longitudinal axis. The trigger may be located on or adjacent a flatter portion of the non-rotationally symmetric cross section. By "flatter", it is intended to mean a portion of the cross section which is less curved or circular than the majority of the cross section. The trigger may be activatable by being pushed inwards into the housing in a direction substantially along the longitudinal axis.

The injection component may be configured to dispense the fluid out of the discharge nozzle when in the injection position. The injection component may be configured to dispense the fluid out of the discharge nozzle only when in the injection position. The injection component may be configured to move from its injection position to a retracted position after the fluid has been dispensed. The housing may comprise a moveable discharge nozzle protector which is configured to extend from the housing fully over the discharge nozzle when in its injection position after the fluid has been dispensed.

The housing may additionally have a portion which is non-axially symmetric at the proximal end of the housing.

The non-rotationally symmetric cross section of the housing may extend over at least 2%, 5%, 10%, 20%, 30%, 40%, 50%, 60%, 70%, 80%, 90%, or 100% of the housing when in its pre-injection position. The non-rotationally symmetric cross section at one or more locations along the longitudinal axis may have a partial circular or elliptical section about its circumference.

The partial circular section may form at least 5%, 10%, 20%, 30%, 40%, 50%, 60%, 70%, 80%, 90%, or 95% of the circumference of the non-rotationally symmetric cross section at one or more locations along the longitudinal axis. The proportion of the partial circular or elliptical section of the circumference of the non-rotationally symmetric cross section may increase along the length of the housing from the proximal to the distal end. The proportion of the partial circular or elliptical section of the circumference of the non-rotationally symmetric cross section may increase continuously along the length of the housing from the proximal to the distal end.

The proportion of the partial circular or elliptical section of the circumference of the non-rotationally symmetric cross section may increase along the length of the housing from the proximal to the distal end from 0% to at least 50%, 60%, 70%, 80%, 90%, 95%, or 100%.

The non-rotationally symmetric cross section at one or more locations along the longitudinal axis may have a linear section on its circumference. The linear section may be tangential to the longitudinal axis. The linear section may form at least 5%, 10%, 20%, 30%, 40%, or 50% of the circumference of the non-rotationally symmetric cross section at one or more locations along the longitudinal axis.

The housing comprises a planar section at the proximal end which is angled at an angle less than 90 degrees relative to the longitudinal axis. This planar section can form a finger grip.

In a second aspect, there is provided an injection device, comprising:

a housing having a proximal end, a distal end, and a longitudinal axis extending between the proximal end and the distal end;

an injection component including a discharge nozzle, wherein the discharge nozzle is comprised fully within the housing in a pre-injection position, wherein the discharge nozzle in an injection position extends partially or fully from the housing along the longitudinal axis at the distal end of the housing, wherein the distal end defines a skin-contacting portion having a cross-section that is substantially circular, and the proximal end defines a proximal cross section including a first, substantially circular portion truncated by a second, substantially flattened portion.

The proximal end may further define a thumb rest portion including a curved corner that extends into the second, substantially flattened portion of the proximal cross section.

The injection device may further comprise a viewing window on a side of the injection device which does not form part of the hand grip portion, wherein the viewing window enables a user to view the injection component and its contents. The viewing window enables viewing of the injection component from an external location to the device and viewing of the contents of the injection component when a user's hand is in place on the hand grip portion. The viewing window may be located on the housing at a position about the device's longitudinal axis which is rotated with respect to the thumb rest portion. The position of the viewing window, e.g. centre axis of the window taken in a circumferential position around the housing, may be located at a position which is rotated from the position of the thumb rest portion, e.g. centre point taken in a circumferential position around the housing, in the range of 45 to 135 degrees, 60 to 120 degrees, or 80 to 100 degrees, or substantially 90 degrees.

The injection device of any of the aforementioned aspects may be configured for delivery of one or more of the following pharmacological products: SIMPONI, STELARA, TREMFAYA, and EPREX. The injection component may comprise one of the aforementioned products and is configured for subcutaneous injection of the product via the discharge nozzle.

The injection device of any of the aforementioned aspects may be configured for delivery of one or more of the following: antibodies (such as monoclonal antibodies, ustekinumab, golimumab, infliximab, guselkumab, sirukumab, adalimumab, rituximab, tocilizumab, certolizumab, certolizumab pegol, sarilumab, secukinumab, ixekizumab or biosimilar versions thereof), etanercept, abatacept, anakinra, epoetin alfa, darbepoetin alfa, epoetin beta-methoxy polyethylene glycol, peginesatide, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying anti-rheumatic drugs, erythropoietin, or vaccines. The injection component may comprise one of the aforementioned products and is configured for injection of the product via the discharge nozzle.

BRIEF DESCRIPTION OF DRAWINGS

The present invention is described below by example with reference to the accompanying figures in which.

DETAILED DESCRIPTION

With reference to FIGS. 1 to 7, an injection device 100 of the present invention is described according to an illustrative embodiment below.

Figure 1:
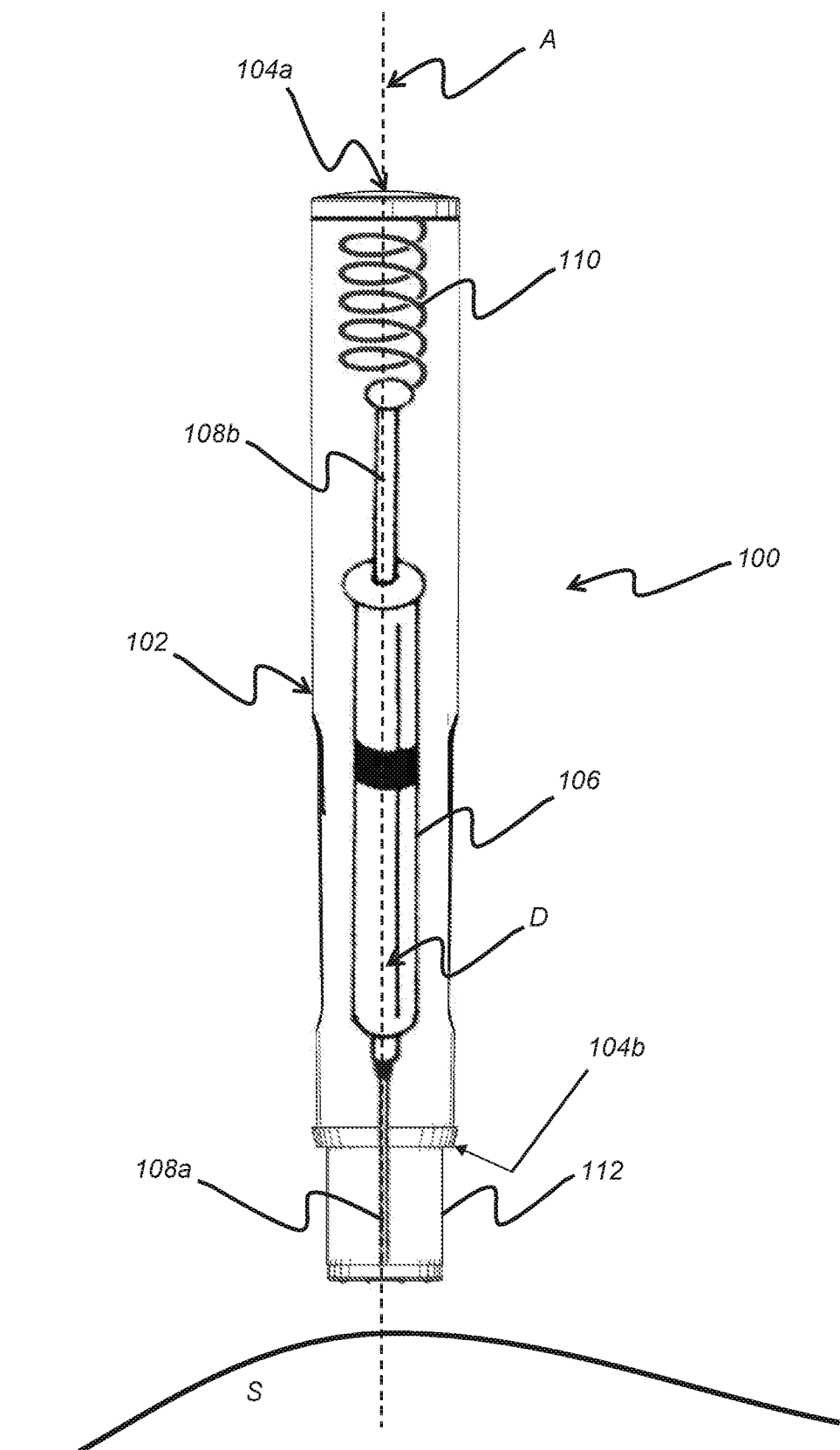
FIG. 1 is schematic representation of the components of an injection device according to the invention.
Figure 2:
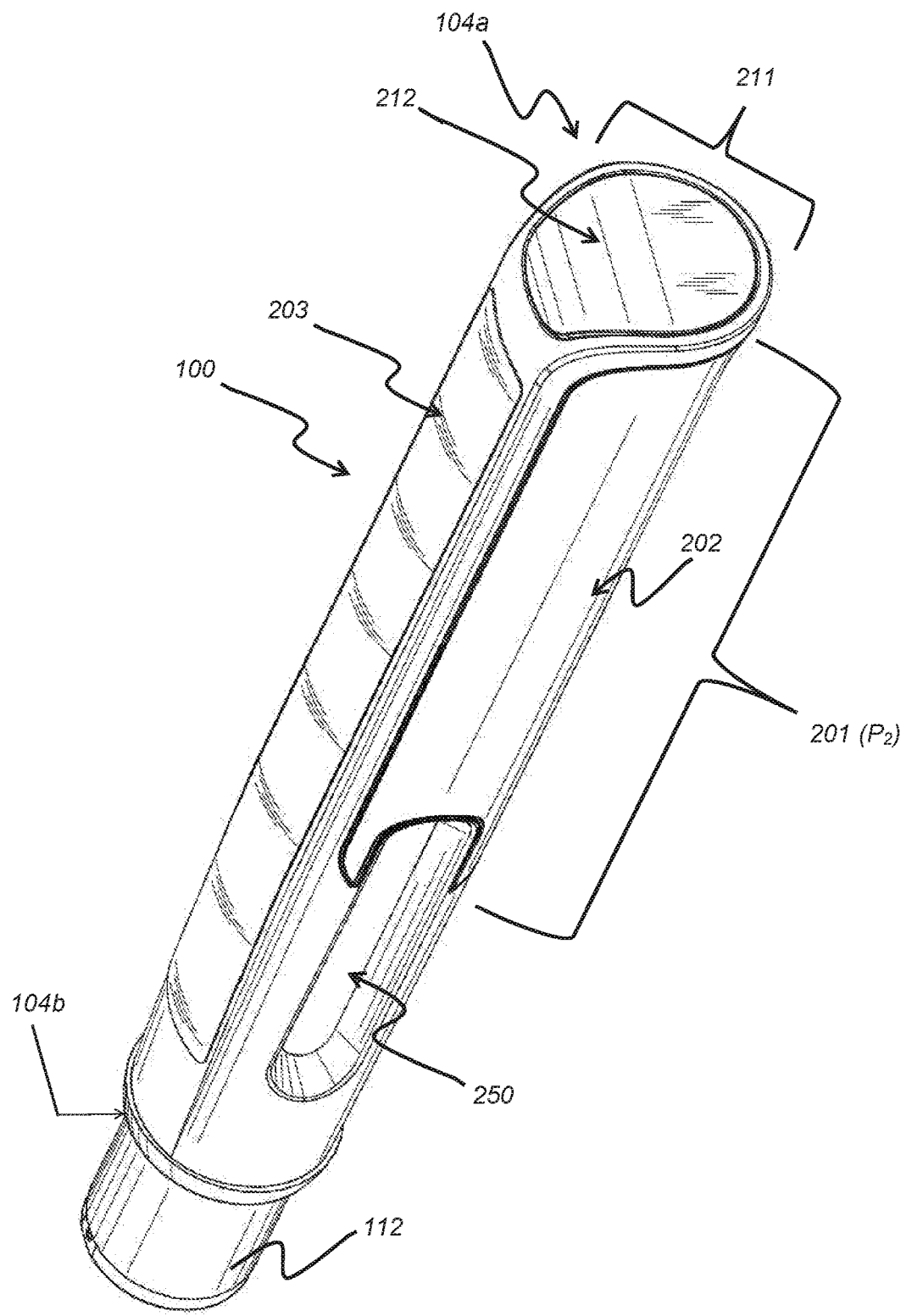
FIG. 2 is a perspective external view of an injection device according to the invention.

As shown in FIG. 1, an injection device 100 according to the invention typically includes a housing 102 having a proximal end 104a, a distal end 104b and a longitudinal axis A extending therebetween. Within the housing 102, there is an injection component 106 having a discharge nozzle 108a, such as a syringe having a needle and a plunger 108b. The syringe holds a drug which is to be delivered into a patient. The housing 102 also contains a drive spring 110 which is arranged upon release to act against the plunger 108b of the syringe to expel the syringe contents D. On the housing 102 is a trigger, which, in the depicted embodiment is a moveable sleeve 112 (or needle protector) at the distal end 104b of the housing 102. Prior to injection, the sleeve 112 fully surrounds the discharge nozzle 108a so that it is protected from causing needle stick injuries.

The sleeve 112 can move into the housing 102, for example when pushed against the skin S of a patient. The needle of the syringe will then insert into the patient's skin S. Once the sleeve 112 has retracted into the housing 102 a given amount and the needle has been pushed to a sufficient skin depth in the skin S, the moveable sleeve 112 releases the drive spring 110 via some internal release mechanism (not shown) so that the drive spring 110 can act against the syringe plunger 108b to cause the drug to be expelled from the syringe into the patient. After injection, during and after removal of the injection device 100 from the skin S of the patient, the sleeve 112 will extend distally across the syringe needle, thereby fully surrounding it. This happens under the action of a return spring (not shown) acting between the sleeve 112 and the housing 102.

Figure 8:
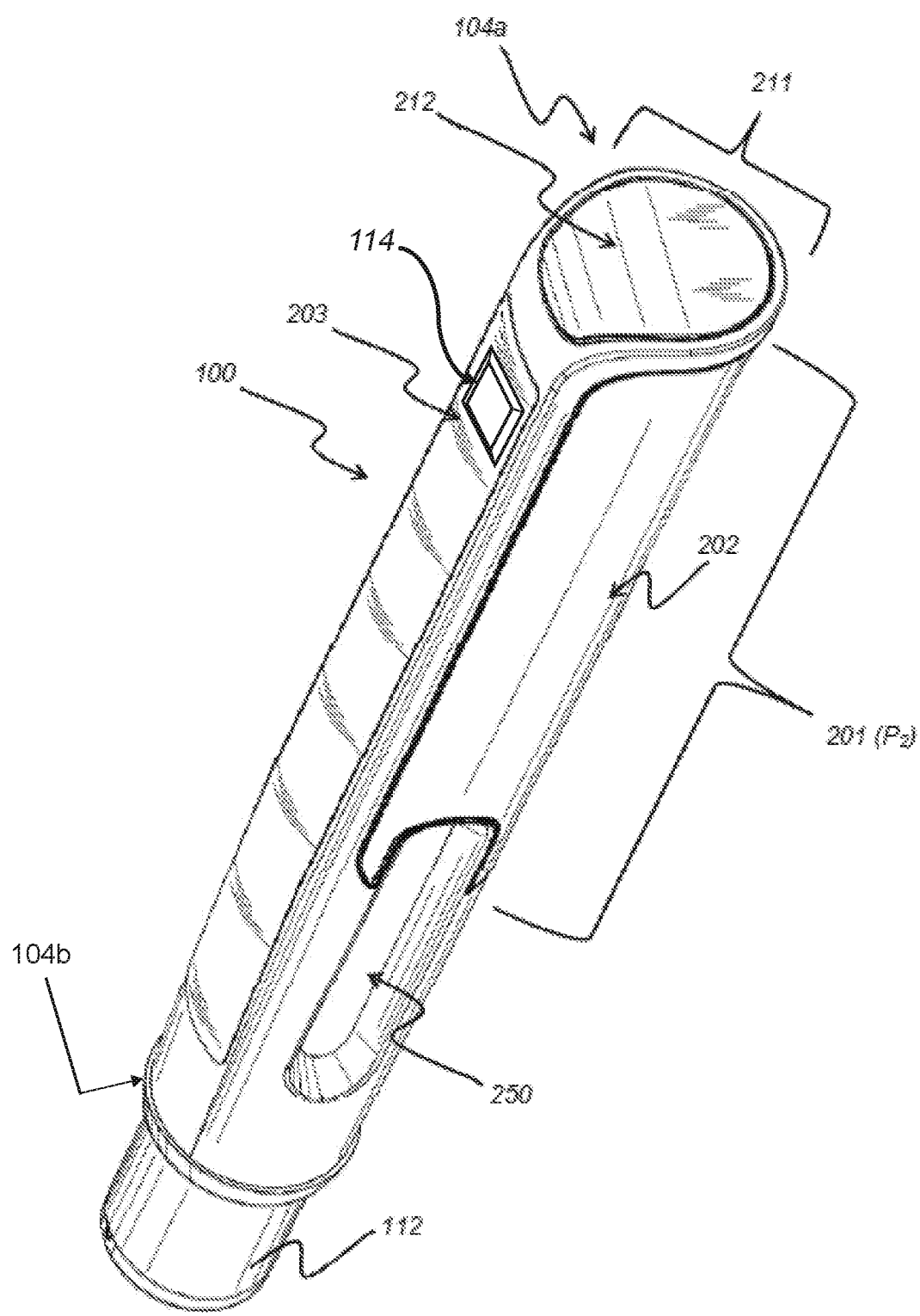
FIG. 8 is a perspective external view of an injection device according to another example of the invention.

In an alternative embodiment (shown in FIG. 8), the trigger may be a separate component of the injection device 100 in addition to the moveable sleeve 112. For example, the trigger may be a button 114 on the side of the injection device 100 which can only be activated once the moveable sleeve 112 has been pushed sufficiently proximally into the device 100 housing 102. In another alternative embodiment, the drive spring 110 may cause the entire syringe body to move distally upon activation of the trigger with the needle of the syringe moving out of the device 100 under the action of the drive spring 110, so as to cause automatic injection, followed by retraction after dispensing of the syringe contents; this being caused by a return spring (not shown) acting on the syringe.

It can thus be seen how the injection device 100 can be operated by a user, who could themselves be the patient, to cause self-administration of the drug. Usability of prior injection devices, i.e. those without the particular non-symmetry mentioned below, is an issue when compared (in confidential patient studies) to the injection device of the present disclosure. Users of these prior injection devices may hold the device upside down, may cover a drug viewing window 250 with their hand, or may hold the device at an angle such that the viewing window is pointed away from them, making it difficult to observe progress of injection and to confirm when the injection is complete prior to lifting the device from the injection site. A problem with prior injection devices also arises when the patient has restricted movement, for example the patient may be elderly, infirm or unwell. For example, the patient may suffer from rheumatoid arthritis or other condition which limits the range of movement of their hand and fingers. The shape and form of the housing 102 of the injection device 100 promotes proper handling and actuation of the injection device 100, for example, by users with restricted movement in their hands and fingers.

Referring to FIGS. 2 to 6, it will be seen that the housing 102 has a hand grip portion 201 formed by a non-rotationally symmetric cross section of the housing 102 about the longitudinal axis A towards the proximal end 104a of the housing 102. The presence of the hand grip portion 201 enables advantageous viewing of a viewing window 250 during operation by a user with their hand placed around the hand grip portion, see particularly FIG. 6. The viewing window 250 is an aperture, or clear or opaque portion of the housing 102 which enables the contents of the injection component 106, e.g. syringe, to be viewed before, after and during operation of the injection device 100. In particular, before operation, the presence of drug D can be checked and viewed. During operation, expulsion of drug D can be seen taking place and the progression of plunger 108b into the syringe can be seen. At and after completion of delivery of drug D, the plunger 108b can be seen fully extended within the syringe, thereby showing to the user that full delivery of drug D has taken place and the injection sequence is complete.

The hand grip portion 201 of the housing 102 is formed to fit within a user's hand H during operation of the device 100, particularly during an injection sequence. As can be seen from FIGS. 2 to 6, one side of the hand grip portion 201 forms a flatter (linear) shaped part 203 of the cross section relative to the other more curved side 202. This flatter portion 203 is thus adapted for receiving fingers of the user's hand when the injection device 100 is being held in the user's hand. The flatter section is substantially tangential to the longitudinal axis A.

The curved portion 202 is generally suited for sitting within a user's palm whilst the device 100 is being gripped. Whilst the exact shape of the hand grip portion 201 shape is not prescribed, it will be seen that the principal requirement is for the cross section to be non-rotationally symmetric such that there are at least two distinct portions having different shapes to the cross section, e.g. two curves of different radii forming each of the flatter and more curved portions on opposing sides to each other. The curved portion 202 may be a partial circle or ellipse.

The curved portion 202 of the hand grip portion 201 is a partial circular or elliptical section forming at least 50% of the circumference of the hand grip portion 201 at one or more locations along the longitudinal axis A, although the exact proportion of the curved portion 202 can vary along the length of the longitudinal axis A. The proportion $P_1$ of the curved portion 202 of the circumference may typically be in the range 50% to 70%, although values outside this range are also possible.

Moreover, the shape and form of the cross section of the hand grip portion 201 varies along the length of the housing 102. Except for the ends of the hand grip portion 201, the variation of cross section happens continuously along the length of the hand grip portion 201. This is to say that there are no discrete or non-continuous jumps in the cross section along the longitudinal axis A. In particular, the proportion of the curved portion 202 may increase along the length of the housing 102 from the proximal to the distal end 104b, whilst the proportion of the flatter section 203 decreases along the length of the housing 102 from the proximal to the distal end 104b.

Figure 7:
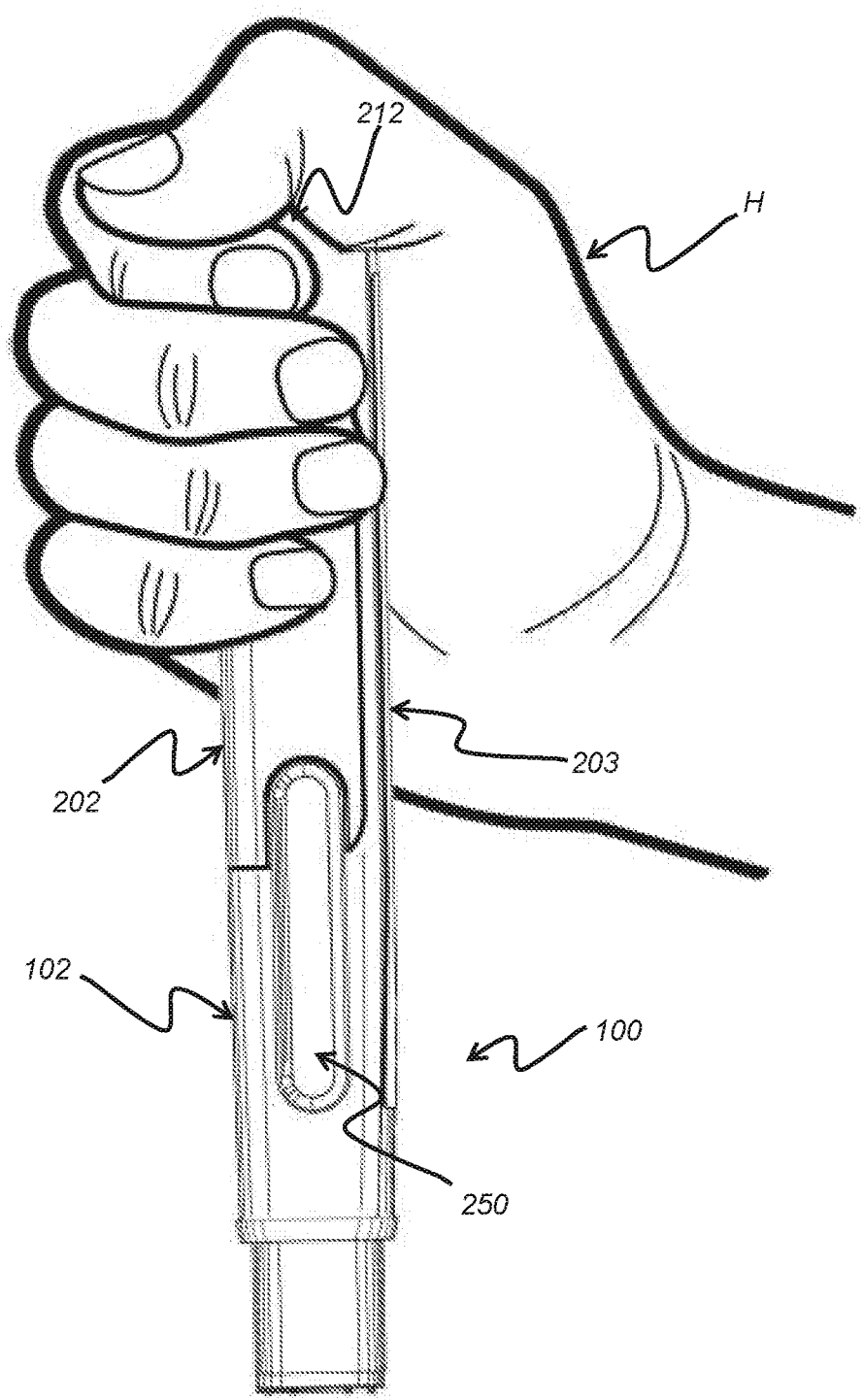
FIG. 7 is a view of the injection device of FIG. 2 with a user's hand in place around the injection device.

The housing 102 also comprises a thumb rest portion 211 which is located on the proximal end 104a of the device 100. The thumb rest portion 211 is located on the opposite side of housing 102 to the curved portion 202 of the hand grip portion 201; this enables effective grip of the device 100 by a user's hand H. This thumb rest portion 211 comprises a curved surface 212 which curves from the planar surface 212 at the proximal end 104a of the device 100 around the proximal end of the device 100 and along the housing 102 into the flat (linear) shaped part 203 of the cross section. This curved surface 212 fits snuggly under the thumb of the user when their hand is in place around the hand grip portion 201. Alternatively or in addition, the thumb rest portion may comprise a planar surface which is angled with respect to the longitudinal axis A of the housing 102; this means that the planar surface 212 is angled at an angle A less than 90 degrees relative to the longitudinal axis A. Thus, with either the planar surface and/or the curved portion of the thumb rest portion 211, the thumb rest portion 211 is accordingly shaped to receive a thumb of the user's hand H, particularly when the device 100 is being gripped by a user with their hand H around the hand grip portion 201, as shown in FIG. 7.

Overall, the provision of either or both of the hand grip portion 201 and thumb rest portion 211 much improved recognition for handling of the device and enable stable holding of the device 100, particularly for users with limited dexterity and particularly during use of the device 100, e.g. during placement on a patient's skin S and during activation and injection. In particular, the non-symmetric flat shaped portion of the proximal end, which is located away from the injection end (which, in contrast, has a symmetric cross section), means that a user can intuitively recognise which end is to be used for gripping the injection device and where their hand is to be placed.

Figure 3:
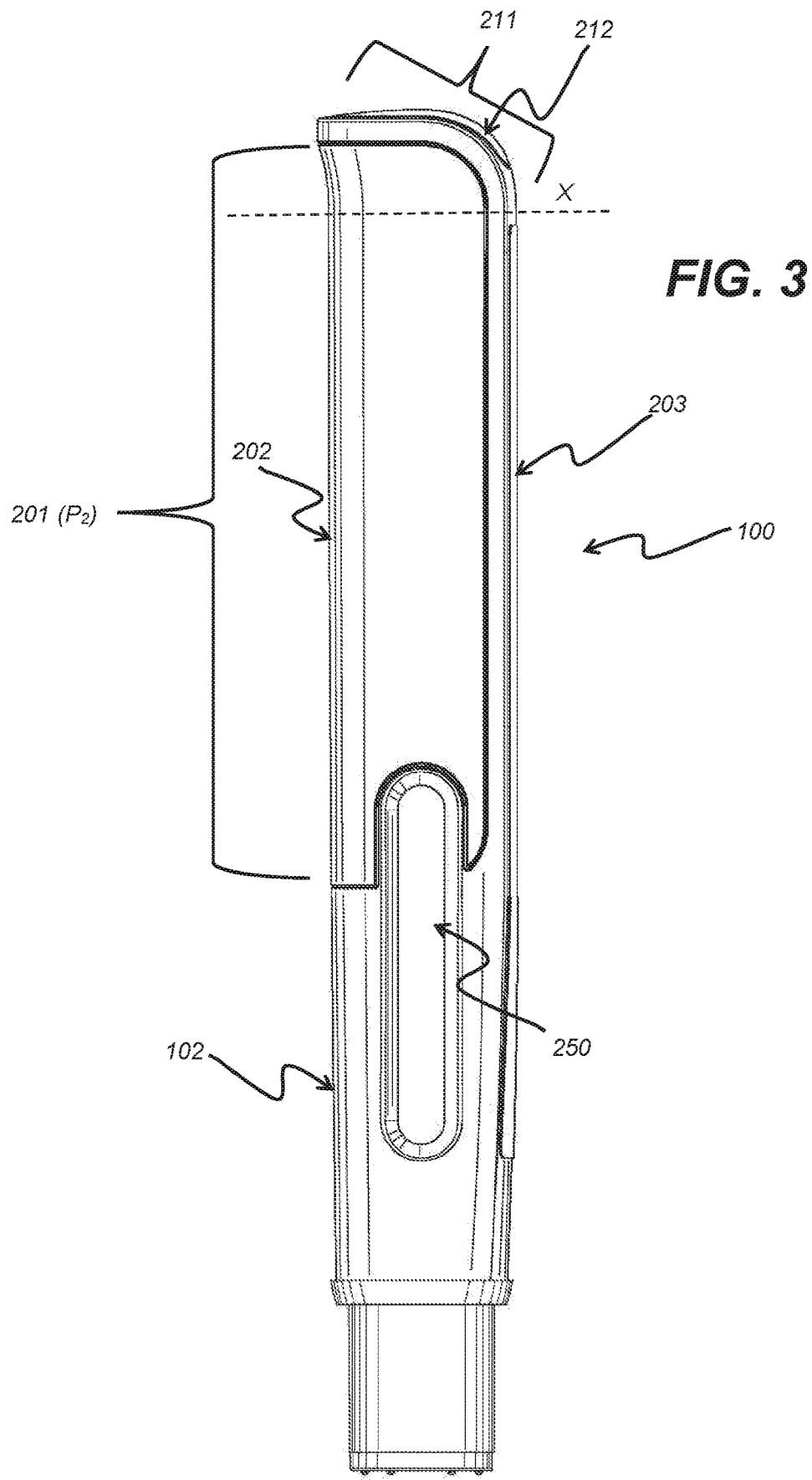
FIG. 3 is side view of the injection device of FIG. 2.
Figure 4:
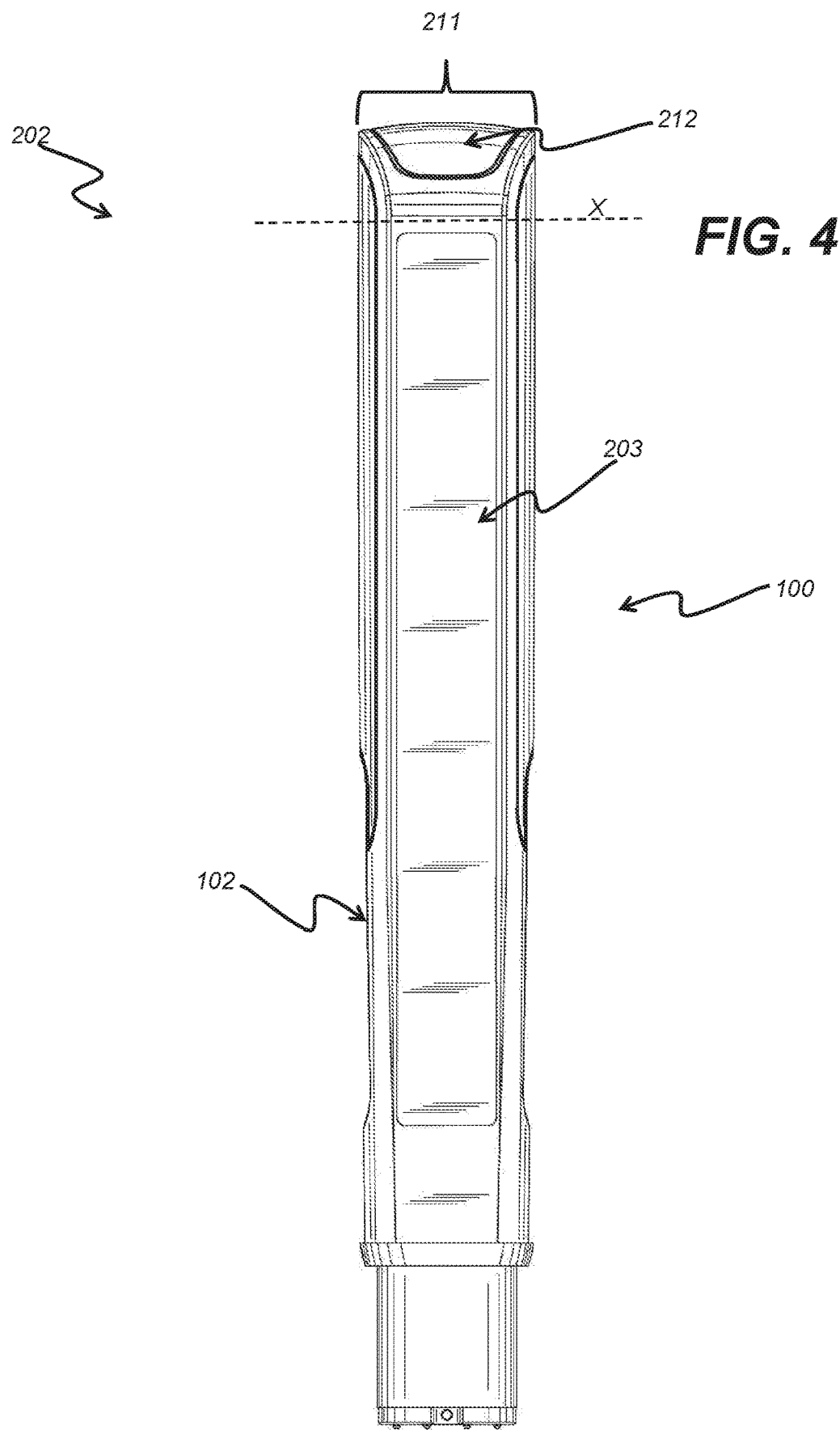
FIG. 4 is a top plan view of the injection device of FIG. 2.
Figure 5:
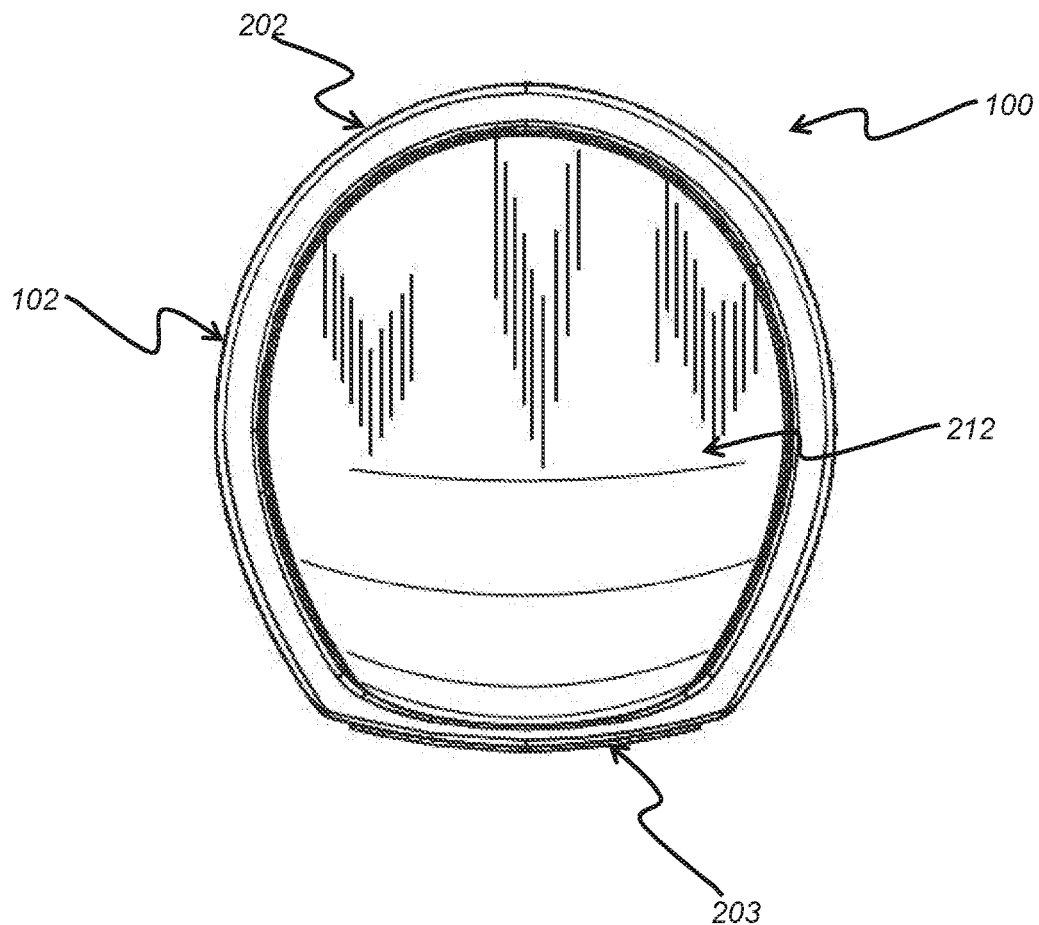
FIG. 5 is an end view of the injection device of FIG. 2.
Figure 6:
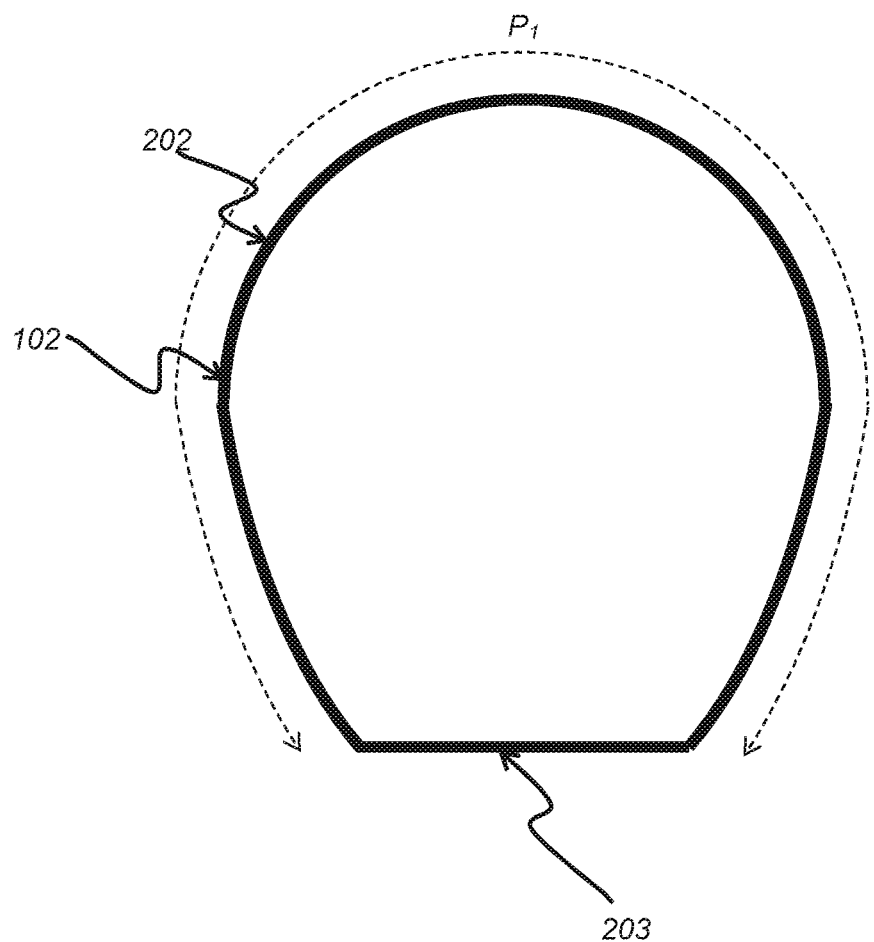
FIG. 6 is a cross-sectional view of the injection device of FIG. 2 along line X shown in FIGS. 3 and 4.

It can be seen from FIG. 3 how the hand grip portion 201 of the housing 102 extends over at least 40% of the housing 102 along its longitudinal axis A (when in its pre-injection position). The proportion $P_2$ of the hand grip portion 201 relative to the entire length of the injection device 100 may typically be in the range 30% to 60%, although the proportion $P_2$ may also sit outside this range and still provide for enhanced grip on the injection device 100.

Numbered Embodiments of the Invention

1. According to an embodiment of the invention, there is provided an injection device, comprising:
   a housing having a proximal end, a distal end and a longitudinal axis extending therebetween,
   an injection component including a discharge nozzle,
   wherein the discharge nozzle is comprised fully within the housing in a pre-injection position,
   wherein the discharge nozzle in an injection position extends partially or fully from the housing along the longitudinal axis at the distal end of the housing,
   wherein the housing has a portion with a non-rotationally symmetric cross section about the longitudinal axis at the proximal end of the housing.
2. An injection device, comprising:
   a housing having a proximal end, a distal end, and a longitudinal axis extending between the proximal end and the distal end;
   an injection component including a discharge nozzle,
   wherein the discharge nozzle is comprised fully within the housing in a pre-injection position,
   wherein the discharge nozzle in an injection position extends partially or fully from the housing along the longitudinal axis at the distal end of the housing,
   wherein the distal end defines a skin-contacting portion having a cross-section that is substantially circular, and the proximal end defines a proximal cross section including a first, substantially circular portion truncated by a second, substantially flattened portion.
3. The injection device of embodiment 2, wherein the proximal end further defines a thumb rest portion including a curved corner that extends into the second, substantially flattened portion of the proximal cross section.
4. The injection device of embodiment 1 or embodiment 2, wherein the non-rotationally symmetric cross section (embodiment 1) of the housing or proximal cross section (embodiment 2) comprises a hand grip portion shaped to fit within a user's hand.
5. The injection device of embodiment 4, wherein an opposing side of the housing to the hand grip portion forms a flatter shaped part of the cross section relative to the grip portion for receiving fingers of the user's hand when the injection device is being held in the user's hand.
6. The injection device of embodiment 4 or embodiment 5, further comprising a thumb rest portion shaped to receive a thumb of the user's hand.
7. The injection device of any one of the preceding embodiments further comprising a discharge nozzle protector, wherein the discharge nozzle protector moves between a position entirely covering the discharge nozzle when in the pre-injection position to a retracted position in which the discharge nozzle is partially or fully exposed.
8. The injection device of any one of embodiments 1 to 6, wherein the injection component is moveable within the housing between the pre-injection position and the injection position.
9. The injection device of embodiment 8, comprising a drive mechanism and a trigger, wherein the injection component is moveable automatically upon activation of the drive mechanism.
10. The injection device of embodiment 9, wherein the trigger is located at the proximal end of the housing.
11. The injection device of embodiment 10, wherein the trigger is activatable by being pushed inwards into the housing in a direction substantially along the longitudinal axis.
12. The injection device of embodiment 9, wherein the trigger is located on a side of the housing and is activatable by being pushed in part inwards into the housing in a radial direction relative to the longitudinal axis.
13. The injection device of embodiment 12, wherein the trigger is located on or adjacent an asymmetric portion of the non-rotationally symmetric cross section.
14. The injection device of embodiment 10, wherein the trigger is activatable by being pushed inwards into the housing in a direction substantially along the longitudinal axis.
15. The injection device of any one of the preceding embodiments, wherein the injection component is configured to dispense to fluid out of the discharge nozzle when in the injection position.
16. The injection device of any one of the preceding embodiments, wherein the injection component is configured to dispense to fluid out of the discharge nozzle only when in the injection position.
17. The injection device of embodiment 15 or embodiment 16, wherein the injection component is configured to move from its injection position to a retracted position after the fluid has been dispensed.
18. The injection device of embodiment 15 or embodiment 16, wherein the housing comprises a moveable discharge nozzle protector which is configured to extend from the housing fully over the discharge nozzle when in its injection position after the fluid has been dispensed.
19. The injection device of any one of the preceding embodiments, wherein the non-rotationally symmetric cross section of the housing (embodiment 1) extends over at least 2%, 5%, 10%, 20%, 30%, 40%, 50%, 60%, 70%, 80%, 90%, or 100% of the housing when in its pre-injection position, or the proximal cross section of the housing (embodiment 2)

extends over at least 2%, 5%, 10%, 20%, 30%, 40%, 50%, 60%, 70% of the housing when in its pre-injection position.

20. The injection device of any one of the preceding embodiments, wherein the non-rotationally symmetric cross section (embodiment 1) or proximal cross section (embodiment 2) at one or more locations along the longitudinal axis has a partial circular or elliptical section about its circumference.

21. The injection device of embodiment 20, wherein the partial circular section forms at least 5%, 10%, 20%, 30%, 40%, 50%, 60%, 70%, 80%, 90%, or 95% of the circumference of the non-rotationally symmetric cross section at one or more locations along the longitudinal axis.

22. The injection device of embodiment 20 or embodiment 21, wherein the proportion of the partial circular or elliptical section of the circumference of the non-rotationally symmetric/proximal cross section increases along the length of the housing from the proximal to the distal end.

23. The injection device of embodiment 20 or embodiment 21, wherein the proportion of the partial circular or elliptical section of the circumference of the non-rotationally symmetric/proximal cross section increases continuously along the length of the housing from the proximal to the distal end.

24. The injection device of embodiment 20 or embodiment 21, wherein the proportion of the partial circular or elliptical section of the circumference of the non-rotationally symmetric/proximal cross section increases along the length of the housing from the proximal to the distal end from 0% to at least 50%, 60%, 70%, 80%, 90%, 95%, or 100%.

25. The injection device of any one of the preceding embodiments, wherein the non-rotationally symmetric/proximal cross section at one or more locations along the longitudinal axis has a linear section on its circumference.

26. The injection device of embodiment 25, wherein the linear section is tangential to the longitudinal axis.

27. The injection device of embodiment 25 or embodiment 26, wherein the linear section forms at least 5%, 10%, 20%, 30%, 40%, or 50% of the circumference of the non-rotationally symmetric/proximal cross section at one or more locations along the longitudinal axis.

28. The injection device of any one of the preceding embodiments, wherein the housing comprises a planar section at the proximal end which is angled at an angle less than 90 degrees relative to the longitudinal axis.

29. The injection device of embodiment 4 and subsequent embodiments, further comprising a viewing window on a side of the injection device which does not form part of the hand grip portion, wherein the viewing window enables a user to view the injection component and its contents.

30. The injection device of any of the aforementioned embodiments, wherein the injection device is configured for delivery of one or more of the following pharmacological products: SIMPONI, STELARA, TREMFAYA, and EPREX.

31. The injection device of embodiment 30, wherein the injection component comprises one of the aforementioned pharmacological products and is configured for subcutaneous injection of the pharmacological product via the discharge nozzle.

32. The injection device of any of the aforementioned embodiments, wherein the injection device is configured for delivery of one or more of the following: antibodies (such as monoclonal antibodies, ustekinumab, golimumab, infliximab, guselkumab, sirukumab, adalimumab, rituximab, tocilizumab, certolizumab, certolizumab pegol, sarilumab, secukinumab, ixekizumab or biosimilar versions thereof), etanercept, abatacept, anakinra, epoetin alfa, darbepoetin alfa, epoetin beta-methoxy polyethylene glycol, peginesatide, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying antirheumatic drugs, erythropoietin, or vaccines.

33. The injection device of claim 32, wherein the injection component comprises one of the aforementioned pharmacological products and is configured for subcutaneous injection of the pharmacological product via the discharge nozzle.

It will be appreciated that the present invention has been described above by way of example only and that modifications of detail can be made with the scope and spirit of the invention which is defined in the appendant claims.

The invention claimed is:

1. An injection device, comprising:
    a housing having a proximal end, a distal end and a longitudinal axis extending therebetween,
    an injection component including a discharge nozzle,
    wherein the discharge nozzle is comprised fully within the housing in a pre-injection position,
    wherein the discharge nozzle in an injection position extends partially or fully from the housing along the longitudinal axis at the distal end of the housing,
    wherein the housing has a portion with a non-rotationally symmetric cross section about the longitudinal axis at the proximal end of the housing,
    wherein the non-rotationally symmetric cross section has a flatter section attached on both sides to a partial circular or elliptical section about its circumference at one or more locations along the longitudinal axis, and
    wherein a proportion of the flatter section decreases along a distal direction that extends from the proximal end towards the distal end such that a proportion of the partial circular or elliptical section of the circumference of the non-rotationally symmetric cross section increases along the distal direction.

2. The injection device of claim 1, wherein the non-rotationally symmetric cross section of the housing comprises a hand grip portion shaped to fit within a user's hand.

3. The injection device of claim 2, wherein an opposing side of the housing to the hand grip portion forms the flatter part of the non-rotationally symmetric cross section relative to the hand grip portion for receiving fingers of the user's hand when the injection device is being held in the user's hand.

4. The injection device of claim 2, further comprising a thumb rest portion shaped to receive a thumb of the user's hand.

5. The injection device of claim 2, further comprising a viewing window on a side of the injection device which does not form part of the hand grip portion, wherein the viewing window enables a user to view the injection component and its contents.

6. The injection device of claim 1, further comprising a discharge nozzle protector, wherein the discharge nozzle protector moves between a position entirely covering the discharge nozzle when in the pre-injection position to a retracted position in which the discharge nozzle is partially or fully exposed.

7. The injection device of claim 1, wherein the injection component is moveable within the housing between the pre-injection position and the injection position.

8. The injection device of claim 7, comprising a drive mechanism and a trigger, wherein the injection component is moveable automatically upon activation of the drive mechanism.

9. The injection device of claim 8, wherein the trigger is located at the proximal end of the housing.

10. The injection device of claim 9, wherein the trigger is activatable by being pushed inwards into the housing in a direction substantially along the longitudinal axis.

11. The injection device of claim 8, wherein the trigger is located on a side of the housing and is activatable by being pushed in part inwards into the housing in a radial direction relative to the longitudinal axis.

12. The injection device of claim 11, wherein the trigger is located on or adjacent an asymmetric portion of the non-rotationally symmetric cross section.

13. The injection device of claim 1, wherein the injection component is configured to dispense fluid out of the discharge nozzle when in the injection position.

14. The injection device of claim 13, wherein the injection component is configured to dispense fluid out of the discharge nozzle only when in the injection position.

15. The injection device of claim 13, wherein the injection component is configured to move from its injection position to a retracted position after the fluid has been dispensed.

16. The injection device of claim 13, wherein the housing comprises a moveable discharge nozzle protector which is configured to extend from the housing fully over the discharge nozzle when in its injection position after the fluid has been dispensed.

17. The injection device of claim 1, wherein the non-rotationally symmetric cross section of the housing extends over at least 2%, 5%, 10%, 20%, 30%, 40%, 50%, 60%, 70%, 80%, 90%, or 100% of the housing when in its pre-injection position.

18. The injection device of claim 1, wherein the partial circular section forms at least 5%, 10%, 20%, 30%, 40%, 50%, 60%, 70%, 80%, 90%, or 95% of the circumference of the non-rotationally symmetric cross section at the one or more locations along the longitudinal axis.

19. The injection device of claim 1, wherein the proportion of the partial circular or elliptical section of the circumference of the non-rotationally symmetric cross section increases continuously along a length of the housing from the proximal end to the distal end.

20. The injection device of claim 1, wherein the proportion of the partial circular or elliptical section of the circumference of the non-rotationally symmetric cross section increases along a length of the housing from the proximal end to the distal end from 0% to at least 50%, 60%, 70%, 80%, 90%, 95%, or 100%.

21. The injection device of claim 1, wherein the flatter section is tangential to the longitudinal axis.

22. The injection device of claim 1, wherein the flatter section forms at least 5% 10%, 20%, 30%, 40%, or 50% of the circumference of the non-rotationally symmetric cross section at one or more locations along the longitudinal axis.

23. The injection device of claim 1, wherein the housing comprises a planar section at the proximal end which is angled at an angle less than 90 degrees relative to the longitudinal axis.

24. The injection device of claim 1, wherein the injection device is configured for delivery of one or more of the following pharmacological products: SIMPONI, STELARA, TREMFAYA, and EPREX.

25. The injection device of claim 24, wherein the injection component comprises one of the aforementioned pharmacological products and is configured for subcutaneous injection of the pharmacological product via the discharge nozzle.

26. The injection device of claim 1, wherein the injection device is configured for delivery of one or more of the following: antibodies, etanercept, abatacept, anakinra, epoetin alfa, darbepoetin alfa, epoetin beta-methoxy polyethylene glycol, peginesatide, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying antirheumatic drugs, erythropoietin, or vaccines.

27. The injection device of claim 26, wherein the injection component comprises one of the aforementioned pharmacological products and is configured for injection of the pharmacological product via the discharge nozzle.

28. An injection device, comprising:
a housing having a proximal end, a distal end, and a longitudinal axis extending between the proximal end and the distal end, the proximal and distal ends being positionally fixed relative to one another;
an injection component including a discharge nozzle,
wherein the discharge nozzle is comprised fully within the housing in a pre-injection position,
wherein the discharge nozzle in an injection position extends partially or fully from the housing along the longitudinal axis at the distal end of the housing,
wherein the distal end defines a skin-contacting portion having a cross-section that is substantially circular, and the proximal end defines a proximal non-rotationally symmetric cross section including a first, substantially circular portion truncated by a second, substantially flattened portion,
wherein the second, substantially flattened portion is attached on both sides to the first, substantially circular portion about its circumference at one or more locations along the longitudinal axis, and
wherein a proportion of the second, substantially flattened portion decreases along a distal direction that extends from the proximal end towards the distal end such that a proportion of the first, substantially circular portion of the circumference of the proximal non-rotationally symmetric cross section increases along the distal direction.

29. The injection device of claim 28, wherein the proximal end further defines a thumb rest portion including a curved corner that extends into the second, substantially flattened portion of the proximal non-rotationally symmetric cross section.

30. The injection device of claim 28, wherein the injection device is configured for delivery of one or more of the following pharmacological products: SIMPONI, STELARA, TREMFAYA, and EPREX.

31. The injection device of claim 30, wherein the injection component comprises one of the aforementioned pharmacological products and is configured for subcutaneous injection of the pharmacological product via the discharge nozzle.

32. The injection device of claim 28, wherein the injection device is configured for delivery of one or more of the following: antibodies, etanercept, abatacept, anakinra, epoetin alfa, darbepoetin alfa, epoetin beta-methoxy polyethylene glycol, peginesatide, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying antirheumatic drugs, erythropoietin, or vaccines.

33. The injection device of claim 32, wherein the injection component may comprise one of the aforementioned pharmacological products and is configured for injection of the pharmacological product via the discharge nozzle.

* * * * *